United States Patent [19]

Wilkins, Jr.

[11] Patent Number: 5,856,272
[45] Date of Patent: Jan. 5, 1999

[54] ALGAECIDE COMPOSITIONS AND METHODS OF REMOVING ALGAE

[76] Inventor: Joe S. Wilkins, Jr., 1706 E. Southmore, Pasadena, Tex. 77502

[21] Appl. No.: 558,017

[22] Filed: Nov. 13, 1995

[51] Int. Cl.⁶ .......................... A01N 59/00; A01N 59/20; A01N 27/00

[52] U.S. Cl. .......................... 504/151; 504/152; 424/637; 424/638; 424/665; 514/753

[58] Field of Search ..................................... 514/729, 762, 514/763; 424/630–638, 661–665; 504/151, 152

[56] References Cited

U.S. PATENT DOCUMENTS

| | | | |
|---|---|---|---|
| 4,975,109 | 12/1990 | Friedman, Jr. et al. | 504/122 |
| 5,153,229 | 10/1992 | Chastain et al. | 514/763 |
| 5,164,109 | 11/1992 | Wojtowicz | 252/175 |
| 5,281,280 | 1/1994 | Lisowski et al. | 134/26 |
| 5,294,645 | 3/1994 | Chastain et al. | 514/729 |
| 5,373,025 | 12/1994 | Gay | 514/642 |

*Primary Examiner*—John Pak
*Attorney, Agent, or Firm*—Laura G. Barrow

[57] ABSTRACT

A novel algaecide composition and method of removing algae from a variety of surfaces, in particular a composition comprising at least one terpene and at least one algaecidal agent, is disclosed.

6 Claims, No Drawings

ALGAECIDE COMPOSITIONS AND METHODS OF REMOVING ALGAE

BACKGROUND OF INVENTION

1. Field of Invention

The present invention is related to compositions for removing algae from a variety of surfaces.

2. Description of the Related Art

Especially in hot and humid environments, algae can grow on a variety of surfaces, both interior as well as exterior. The removal of algae from exterior as well as interior surfaces can be a time-consuming and rather unpleasant job, in particular where the surface area to be treated is rather large and/or exceptionally dirty with oil. A common algaecide is sodium hypochlorite. DPC Industries, Inc. of Houston, Texas markets a useful algaecide composition, "DIXICHLOR", which consists of sodium hypochlorite, sodium chloride, sodium hydroxide, and water.

Conventional methods for removing algae comprise spraying an algaecide on the surface containing the algae growth. The algaecidal activity, however, is often diminished where the surface area is dirty, in particular with oily substances. The oils present on the algae-covered surface provide somewhat of a barrier between the algae and the algaecide, thereby minimizing the ability of the algaecide to kill the algae and prevent its further growth. Algaecidal activity could be enhanced by first pre-cleaning the surface with a suitable cleaner, such as a soap and water or a degreaser an/or by hand brushing. However, typically this is not done, and such pre-cleaning can make the job of treating a very large surface area even more difficult and time-consuming.

It would therefore be desireable to have a single algaecide composition comprising both an algaecide and a degreaser that would be especially useful for treating large algae-covered surface areas which are also exceptionally dirty. Examples of surface areas for which such a combination algaecide/degreaser composition would be particularly useful include large exterior patio surfaces and swimming pools in apartment buildings and interior floors in large buildings such as warehouses, for example. The application of a single composition to such surfaces, for example, would save a great deal of time and energy as opposed to first pre-cleaning the entire surface, followed by treating the entire surface with the algaecide.

SUMMARY OF THE INVENTION

The present invention is related to novel compositions for removing algae from a variety of surfaces, both interior and exterior, and methods thereof. In particular, the invention is directed to compositions comprising a combination of a terpene, such as limonene or various terpene hydrocarbon mixtures, and at least one algaecide agent, preferably sodium hypochlorite. The terpene serves as a degreaser to remove oily substances from the algae-covered surface which allows better contact between the algaecidal agent and the algae for better algaecidal results. Such a combination algaecide/degreaser composition is particularly useful where very large and especially dirty surface areas are to be treated, and consequently has a distinct advantage over compositions containing only an algaecide agent.

DETAILED DESCRIPTION OF THE PREFERRED EMBODIMENTS

The inventive algaecidal compositions are aqueous mixtures which preferably contain at least one algaecidal agent, discussed in more detail below, and at least one degreaser, preferably a terpene or combination of terpenes. Terpenes are widely distributed in nature and are present in nearly all living plants. It is generally recognized that the term "terpene" not only applies to isoprene oligomers, but also to their saturated or partially saturated isomers as well as to their derivatives, which are referred to as terpenoids, such as, for example, alcohols, aldehydes, esters, and the like. Terpenes have been widely used as flavor and perfume materials as well as effective cleaning agents for both household and industrial use. Common monoterpenes include turpentine, limonene, and pinene.

The preferred terpenes in the present invention include limonene (e.g. LIMONENE 135 by SGM GLIDCO Organics, of Jacksonville, Fla.) and a combination of terpene hydrocarbons such as DIPENTENE EXTRA (by SGM GLIDCO Organics of Jacksonville, Fla.). Other suitable terpenes include pinene and turpentine. Preferably the inventive algaecide composition comprises from about 0.0025 v/v % to about 0.005 v/v %, more preferably about 0.0025 v/v %, of one or more terpenes.

Due to the aqueous nature of the inventive algaecide composition and the presence of the terpene or terpenes, at least one surfactant is required to solubilize the terpene and thereby provide a homogenous solution. Preferred surfactants include, but are not limited to, polyethoxyethanol non-ionic surfactants; however, any surfactant suitable for solubilizing terpenes may be employed. Examples of such surfactants include, but are not limited to, Triton X-100 and Triton X-114 (octylphenoxy polyethoxy-ethanol), Triton X-110, Triton X-45, and most preferably MAZCLEAN (manufactured by PPG). Preferably, the algaecide composition comprises from about 0.0025 v/v % to about 0.005 v/v % of surfactant, more preferably about 0.0025 v/v %.

The inventive algaecide composition also includes at least one algaecide agent, preferably sodium hypochlorite, in a concentration of from about 3.0 v/v % to about 10 v/v %, more preferably about 5.0 v/v %. While sodium hypochlorite is the most preferred algaecidal agent, other algaecidal agents may also be employed. Preferably an alkali salt, most preferably sodium chloride, is also present in the composition to enhance the algaecidal activity of the sodium hypochlorite. A preferred concentration range of sodium chloride is from about 2.5 v/v % to about 10 v/v %, more preferably about 3.5 v/v %.

The inventive composition also preferably includes an alkali hydroxide, preferably sodium hydroxide, which comprises from about 0.24 v/v % to about 3 v/v %, more preferably from about 0.24 to about 1.0 v/v %, of the composition. The sodium hydroxide is added to activate the algae up and away from the treated surface by a "bubbling" action similar to that of hydrogen peroxide. The sodium hydroxide also causes the terpene component of the composition to "bubble" out and away from the treated surface, thereby allowing easier removal of the terpene (if desired) with soap and water, for example.

In preparing the inventive algaecide composition, no special equipment is needed, however the order of mixing certain components is important. In all cases, it is preferable to add the components to the terpene. In a preferred composition, the terpene or terpene mixture is placed in a mixing vessel. Next, an equal amount of a surfactant is added, with stirring, to the terpene until blended (i.e. the mixture is clear). Next, from about 85 v/v % to about 91 v/v % of water is added slowly, with stirring, to the terpene/surfactant mixture, followed by sodium hypochlorite, sodium hydroxide, and optionally sodium chloride. The sodium hypochlorite, sodium chloride, and sodium hydroxide may be added in any order. Alternatively, a solution comprising the algaecidal agent (e.g. sodium hypochlorite), water, sodium hydroxide and/or sodium chloride can be mixed separately and then slowly added, with stirring, to the terpene/surfactant mixture. The most preferred "pre-mixed" aqueous algaecide composition is the commercial product "DIXICHLOR" vended by DPC Industries, Inc., which comprises about 10% sodium hypochlorite, from about 7% to about 8% sodium chloride, and from about 0.50% to about 2% sodium hydroxide, with the remainder being water.

Preferably, the inventive algaecide composition contains a component to inhibit future algae growth. A suitable algae-growth inhibitor is copper sulfate; however, other algae-growth inhibitors generally known to those of ordinary skill in the art having the benefit of this invention's teachings and suggestions may also be employed. A preferred percentage of copper sulfate ranges from about 0.00099 v/v % to about 0.0012 v/v %, most preferably about 0.00099 v/v %, of the inventive algaecide composition.

The present inventive algaecide composition works well on concrete, pavement, wood, tile, porcelain, vinyl, brick, stucco, fiberglass, and aluminum surfaces. To treat large algae-covered surfaces such as patios, swimming pools, boats and other vehicles, floors, and walls, for example, from about 1.00 gallons to about 1.50 gallons of the inventive composition per about 100 square feet is applied, preferably by spraying, to the surface. The compositions should be allowed to remain on the surface for at least 8 minutes, more preferably for about 10 to 30 minutes, afterwards it may be washed off with water. [It is not necessary to apply the water under pressure by using, for example, a pressure spray gun. Rather, a simple garden hose may be used.] As mentioned above, the inventive algaecide composition is particularly amenable to easy removal from the treated surface via the action of the sodium hydroxide which helps bring the terpene, which is an oily substance itself, to the surface.

Other suitable surfaces include, but are not limited to, basins, showers, bathtubs, and toilet bowls and tanks. In treating the foregoing and similar fixtures, from about 1.0 gallon to about 1.5 gallons of the algaecide composition per about 100 square feet should be used. The inventive composition should preferably remain on the treated surface for a time period ranging from about 8 to about 10 minutes, and afterwards it may washed off with water.

The present inventive algaecide composition may also be used in combination with a solution of 3% hydrogen peroxide to treat a surface. The purpose of the hydrogen peroxide is to move the terpene component of the applied algaecide composition up to the treated surface via a "bubbling action" for easy water removal thereof. It is important that if hydrogen peroxide is to be used, that it is not mixed directly with the algaecide composition, but rather applied separately to the surface to be treated. [If the hydrogen peroxide is first mixed with the algaecide composition, the peroxide gas will release immediately and then stop, thereby defeating its purpose.] Preferably, a special spray apparatus containing two separate lines, for example, is used in this particular embodiment, whereby one line contains the algaecide composition and a separate line contains hydrogen peroxide. After about two minutes, the solutions may be washed off with water. Alternatively, the algaecide composition may be applied first to the particular surface, followed by the hydrogen peroxide solution. After about two minutes, the solutions may be washed off with water.

The following examples are not intended to limit the scope of the invention, but are intended to illustrate the various aspects of the invention.

EXAMPLE 1

Manufacture of inventive algaecide composition

About 27 gallons of water was added to approximately 27 gallons of concentrated DIXICHLOR (i.e. 10% sodium hypochlorite; 7–8% sodium chloride; 0.5–2% sodium hydroxide; and 80% water] in a 55gallon drum to form Solution A. Next, about two liters (i.e. 0.54 gallons) of Solution B was prepared, by combining the following components, with stirring, until blended: 5.0 ml of LIMONENE #135 (SGM GLIDCO Organics), 5.0 ml of of MAZCLEAN (by PPG), 2.0 ml of copper sulfate, about 1,000 ml of concentrated DIXICHLOR, and the about 1,000 ml of water. Solution B was added to Solution A, with stirring, until blended.

EXAMPLE 2

Manufacture of inventive algaecide composition

About 27 gallons of water was added to approximately 27 gallons of concentrated DIXICHLOR (i.e. 10% sodium hypochlorite; 7–8% sodium chloride; 0.5–2% sodium hydroxide; and 80% water] in a 55-gallon drum to form Solution A. Next, about two liters (i.e. 0.54 gallons) of Solution B was prepared, by combining the following components, with stirring, until blended: 5.0 ml of DIPENTENE EXTRA (SGM GLIDCO Organics), 5.0 ml of of MAZCLEAN (by PPG), 2.0 ml of copper sulfate, about 1,000 ml of concentrated DIXICHLOR, and the about 1,000 ml of water. Solution B was added to Solution A, with stirring, until blended.

EXAMPLE 3

The algaecide composition of Example 1 was applied to a brick surface. After about 10 minutes, the applied algaecide composition was washed off with water using a water hose.

EXAMPLE 4

A brick surface was treated with a combination of the algaecide composition of Example 1 and a 3% solution of hydrogen peroxide. About 128 ounces of the algaecide composition of Example 1 and about 25.6 ounces of the hydrogen peroxide solution were prepared in separate vessels, which in turn were connected to a spray gun. The two solutions were then sprayed simultaneously onto the brick surface. After about two minutes, the solutions were washed off with water.

I claim:

1. A composition suitable for use as an algaecide comprising limonene, sodium hypochlorite, and copper sulfate.

2. The composition of claim 1, wherein said composition comprises from about 0.0025 to about 0.005 v/v % of limonene, from about 3 to about 10 v/v % of sodium hypochlorite, and from about 0.00099 to about 0.0012 v/v % copper sulfate.

3. The composition of claim 2, wherein said composition further includes from about 3 to about 8 v/v % sodium chloride, from about 0.24 to about 3 v/v % sodium hydroxide, and from about 85 to about 91 v/v % water.

4. A method for removing algae from a surface comprising the step of applying an algaecidal composition to said surface, wherein said composition comprises limonene, sodium hypochlorite, and copper sulfate.

5. The method of claim 4, wherein said composition comprises from about 0.0025 to about 0.005 v/v % limonene, from about 3 to about 10 v/v % sodium hypochlorite, and from about 0.00099 to about 0.0012 v/v % copper sulfate.

6. The method of claim 5, wherein said composition further includes from about 3 to about 8 v/v % sodium chloride, from about 0.24 to about 3 v/v % sodium hydroxide, and from about 85 to about 91 v/v % water.

* * * * *